United States Patent [19]
Scholz et al.

[11] Patent Number: 6,114,510
[45] Date of Patent: Sep. 5, 2000

[54] PROCESS FOR THE PURIFICATION OF RECOMBINANT HUMAN INTERLEUKIN-8

[75] Inventors: Peter Scholz; Peter Donner; Joachim Daum; Werner Boidol, all of Berlin; Andre Koltermann, Göttingen, all of Germany

[73] Assignee: Schering Aktiengesellschaft, Germany

[21] Appl. No.: 09/077,757

[22] PCT Filed: Dec. 11, 1996

[86] PCT No.: PCT/EP96/05540

§ 371 Date: Jun. 11, 1998

§ 102(e) Date: Jun. 11, 1998

[87] PCT Pub. No.: WO97/21813

PCT Pub. Date: Jun. 19, 1997

[30] Foreign Application Priority Data

Dec. 12, 1995 [EP] European Pat. Off. ............ 195 48 630

[51] Int. Cl.$^7$ ................. C07K 1/14; C07K 1/16; C07K 1/18; C07K 14/00
[52] U.S. Cl. .......... 530/412; 530/414; 530/416; 530/418; 435/70.1; 435/71.1
[58] Field of Search ................. 530/351, 412, 530/414, 416, 418; 435/70.1, 71.1

[56] References Cited

U.S. PATENT DOCUMENTS

| | | | |
|---|---|---|---|
| 4,599,176 | 7/1986 | Wittenberger | 210/639 |
| 5,302,384 | 4/1994 | Gimbrone, Jr. et al. | 424/85.2 |

FOREIGN PATENT DOCUMENTS 9108483  6/1991  WIPO.

OTHER PUBLICATIONS

Furuta et al., *J. Biochem.*, vol. 106, pp. 436–441 (1989).
Ricketts et al., *American Chemical Society, Washington*, vol. 271, pp. 21–49 (1985).
Van Damme et al., *Journal of Experimental Medicine*, vol. 167, No. 4, pp. 1364–1376 (1988).
Tutunjian, *Biotechnology*, vol. 3, pp. 615–626 (1985).

*Primary Examiner*—Elizabeth Kemmerer
*Assistant Examiner*—Nirmal S. Basi
*Attorney, Agent, or Firm*—Millen, White, Zelano & Branigan, P.C.

[57] ABSTRACT

A process is described for the purification of recombinant interleukin-8, which allows the production of interleukin-8 under Good Manufacturing Practice (GMP) conditions.

36 Claims, 2 Drawing Sheets

PROCESS FOR THE PURIFICATION OF RECOMBINANT HUMAN INTERLEUKIN-8

This application is a 371 of PCT/EP96/05540 filed Dec. 11, 1996.

FIELD OF THE INVENTION

The present invention relates to a process for the purification of recombinant human interleukin-8 that has been obtained in various ways.

SUMMARY OF THE INVENTION

Processes for the purification of recombinant human interleukin-8 are already known. Various study groups have developed different purification processes. The purification differs essentially in the chromatography steps chosen, the following methods having been described: Mono S with subsequent reversed phase HPLC (Lindley, I.; Aschauer, H.; Seifert, J.-M.; Lam, C.; Brunowski, W.; Kownatzki, E.; Thelen, M.; Peveri, P.; Dewald, B.; von Tscharner, V.; Walz, A.; Baggiolini, M. (1988): Synthesis and expression in E. coli of the gene encoding monocyte-derived neutrophil-activating factor: Biological equivalence between natural and recombinant neutrophil-activating factor. Proceedings of the National Academy of Science, USA, 85), DEAE Sephacel throughflow for heparin Sepharose followed by Sephacryl S-200 and CM-3SW column (Matsushima, K.; Oppenheimer, J. J. (1989): Interleukin-8 and MCAF: novel inflammatory cytokines inducible by IL 1 and TNF. Cytokine 1), CM-Sepharose CL-6B with subsequent Toyopearl HW-55 (Furuta, R.; Yamagishi, J.; Kotani, H.; Sakamoto, F.; Fukui, T.; Matsui, Y.; Sohmura, Y.; Yamada, M.; Yoshimura, T.: Larsen, C. G.; Oppenheim, J. J.; Matsushima, K. (1989): Production and characterization of recombinant human neutrophil chemotactic factor. Journal of Biochemistry, Vol. 106, No. 3) and batch adsorption with silicate acid followed by heparin Sepharose CL-6B and Utrogel AcA 54 (Van Damme, J.; Van Beeumen, J.; Conings, R.; Decock, B.; Billau, A. (1989): Purification of granulocyte chemotactic peptide/interleukin-8 reveals N-terminal sequence heterogeneity similar to that of β-thromboglobulin, European Journal of Biochemistry 181). Downstream processing for the production of interleukin-8 under GMP conditions on a commercial scale is not known.

Disadvantages of the known processes are low yield and the lack of purity of interleukin-8 with, at the same time, high material costs. A further disadvantage of the known processes is their use only for research purposes, that it to say their inability to be translated to production methods conforming to GMP.

A process for the purification of recombinant interleukin-8 has now been developed that overcomes the disadvantages of the known processes.

The process of the invention for the purification of interleukin-8 is characterised in that a) firstly cells are lysed in buffered solution and
b) the resulting lysate is treated by means of molecular weight exclusion by repeated cross-flow ultrafiltration in such a manner that
  i) in the first filtration step interleukin-8 is separated from larger accompanying components and
  ii) in the second filtration step is separated from smaller components,
c) the buffered filtrate from process step b) is subjected to high-resolution purification by means of cation-exchange chromatography, wherein the highly positively charged surface of the interleukin-8 molecule is used in a form such that the application and elution pH value is selected to be sufficiently high that the interleukin-8 can just still bind, then
d) the buffered solution of the interleukin-8 eluate from process step c) is exchanged by gel filtration, dialysis or ultrafiltration and finally
e) the interleukin-8 solution obtained via process step d) is lyophilised.

The cell lysis according to process step a) is necessary only in the case of intracellularly formed protein, with enzymatic (for example by means of lysozyme), chemical (for example by means of organic solvents) and other physical methods of cells lysis (for example by means of ultrasound) also being possible. For commercial cell lysis physical methods are generally preferred (Schewedes and Bunge, 1988 Mechanische Zellaufschlußverfahren, Jahrbuch der Biotechnologie, VCH Verlagsgesellschaft mhB, Weinheim, Germany). Of the physical methods, apart from the ball mill, especially high-pressure homogenisation (Agerkvist and Enfors, 1990, Sauer et al., 1988) may be mentioned as an established and well described method for cell lysis.

The various cell lysis methods mentioned above may be used for the purification process of the invention.

Preferably, high-pressure homogenisation is chosen for process step a) of the process of the invention. Lysis of the cells is effected at a pressure of from 2000 to 15,000 psi and in from 1 to 6 cycles, preferably at a pressure of from 5000 to 7000 psi and in from 3 to 5 cycles, most preferably at a pressure of 6000 psi and in 4 cycles. In that method, more than 95% of cells, such as, for example, E. coli cells, are lysed.

The molecular weight exclusion by repeated cross-flow ultrafiltration according to process step b) may be reduced in principle to filtration with filter modules of 1 and 3 kD NMWL (Nominal Molecular Weight Limit) (Cheryan, M. (1986): Ultrafiltration Handbook, Technomic Publishing Company, Inc., Lancaster, Pa., USA). That filtration is a physical separation method (Vlauck, W. R. A.; Müller, H. A. (1994): Grundoperationen chemischer Verfahrenstechnik, Deutscher Verlag für Grundstoff-industrie, Leipzig, Federal Republic of Germany) and is frequently used in downstream processing for separating off the insoluble portion. Accordingly, cross-flow ultrafiltration is frequently used in downstream processing in separating off whole cells and cell debris and in the separation of inclusion bodies. Examples of separating off soluble accompanying substances, especially accompanying proteins, are described for ultrafiltration on a laboratory scale (Cheryan, M. (1986): Ultrafiltration Handbook, Technomic Publishing Company, Inc., Lancaster, Pa., USA). Commercial use of cross-flow ultrafiltration for separating off soluble accompanying substances is not known, however, and nor is it obvious.

In process step b), a sequential arrangement of two cross-flow ultrafiltrations having different cut offs are used for the separation of a specific molecule size and/or a specific molecular weight range. The arrangement is so selected that, in the first filtration step, interleukin-8 is separated from larger accompanying components and, in the second filtration step, is concentrated and separated from smaller components. In order to obtain as distinct as possible a separation of interleukin-8 and accompanying components various possibilities are available. In the first cross-flow ultrafiltration, it is possible by selecting suitable operating parameters to obtain interleukin-8 in the filtrate of a membrane having a nominally smaller cut off than corresponds to the molecular weight of interleukin-8. Of the operating parameters, the type of membrane and the cut off are the decisive parameters, it being necessary in principle for the interleukin-8 molecule to pass through the membrane. In the process of the invention, the cut off of the membrane should be below the molecular weight of interleukin-8. By altering the operating parameters the cut off increase, with the membrane becoming permeable to interleukin-8.

Preferably, the cross-flow ultrafiltration in the first filtration step i) is carried out with a cut off of 3 kD.

The alteration of the operating parameters may take the form of an increase in the transmembrane pressure for example by increasing the circulating volume or reducing the filtration rate by the addition of additives such as organic solvents, such as propanol, butanol etc., salts, such as sodium chloride, ammonium sulphate etc., chao-tropic agents, such as urea, guanidinium salts, etc., surface-active substances, such as sodium dodecyl sulphate (SDS), Triton®, Tween® etc., or by altering the pH value. The advantage of the process of the invention resides in the possibility of controlling the mass transport of the target molecule through the membrane by altering the operating parameters. Before increasing the operating parameters, therefore, the filtrate obtained without the target molecule can be separated off so that, in the further process, some of the accompanying components will already have been separated. In this case, the controlled mass transfer of the interleukin-8 through the membrane can be achieved by increasing the circulating volume.

In the second cross-flow ultrafiltration, a cut off that is smaller than the molecular weight of interleukin-8 can be obtained by selecting suitable operating parameters. In principle, the same possibilities apply here as have already been mentioned in the first cross-flow ultrafiltration. In that case, the interleukin-8 could be separated off from smaller accompanying components by selecting a membrane having a sufficiently small cut off, that is to say by selecting appropriate operating parameters.

The cross-flow ultrafiltration in the second filtration step ii) of process step b) is carried out with a cut off of from 0.1 to 1.5 kD, preferably with a cut off of 1 kD.

In process step c), owing to buffer conditions that result in a highly positive overall charge of interleukin-8, a high-resolution purification step by cation-exchange chromatography is carried out in such a manner that the application and elution pH is selected to be sufficiently high that the interleukin-8 can just still bind. The elution is effected by increasing the sodium chloride concentration in a pH range of from pH 8 to pH 10, preferably at pH 9.5. The advantage of those chromatography conditions lies in a high capacity of the chromatography material, since only very few contaminants (accompanying proteins and endotoxins) are still capable of binding, high purity of the eluate and a high yield.

In the conditioning carried out in process step d), the exchange of the buffered solution of the eluate of interleukin-8 is effected preferably by means of dialysis.

Using the process of the invention it is possible to purify interleukin-8 or recombinant interleukin-8 that has been obtained, for example, using prokaryotic expression systems, such as *E. coli* cells, eukaryotic expression systems, such as yeast cells, especially *Pichia pastoris,* insect cell systems, especially Baculovirus-infected insect cells or permanent insect cell systems, using transformed mammalian cells, such as CHO and BHK, and from the milk of transgenic animals, such as cows ang goats.

Methods of cloning and expressing the gene in the various expression systems are known to the person skilled in the art and may be learned from the relevant literature.

The cross-flow ultrafiltration in the first filtration step i) of process step b) may be carried out in two phases.

Depending upon the construction of the cross-flow ultrafiltration system, specifically the surface area of the filter and the type of membrane, the surface area of the filter may be from 500 to 10,000 cm$^2$ for production scale. The resulting transmembrane pressure $$P_{transmembrane}=(P_{in}-P_{out})/2-P_{filtrate}$$

may accordingly lie in the range of from 1 to 150 psi. The operating parameters circulating volume and filtration rate therefore vary in the ranges of from 1 to 10 l/min and from 1 to 20 ml/min. That applies both to the first and to the second phase of the first filtration step.

Preferably, in the cross-flow ultrafiltration, a circulating volume of from 1 to 4 l/min, a filtration rate of from 5 to 8 ml/min and a transmembrane pressure of from 1 to 20 psi are used in the first phase, and a circulating volume of from 3 to 6 l/min, a filtration rate of from 10 to 15 ml/min and a transmembrane pressure of from 20 to 50 psi are used in the second phase.

Especially preferably, in the ultrafiltration, a circulating volume of from 2 to 3 l/min, a filtration rate of 6.3 ml/min and a transmembrane pressure of 10 psi are used in the first phase, and a circulating volume of from 4 to 5 l/min, a filtration rate of 12.7 ml/min and a transmembrane pressure of 35 psi are used in the second phase.

Also especially preferred in the ultrafiltration is the use of a circulating volume of from 2 to 3 l/min, a filtration rate of 6.3 ml/min and a transmembrane pressure of 10 psi in the first phase, and the use of a circulating volume of from 4 to 5 l/min, a filtration rate of 18.7 ml/min and a transmembrane pressure of 35 psi in the second phase.

The surface area of the filter in that case is preferably 2100 cm$^2$ with a 3 kD cut off.

In the cross-flow ultrafiltration in the second filtration step ii) of process step b), depending upon the type of filter the surface area of the filter may be from 500 to 10,000 cm$^2$. The resulting transmembrane pressure $$P_{transmembrane}=(P_{in}-P_{out})/2-P_{filtrate}$$

may accordingly lie in the range of from 5 to 150 psi. The operating parameters circulating volume and filtration rate will therefore vary in the ranges of from 0.5 to 10 l/min and from 1 to 20 ml/min.

Preferably, in the cross-flow ultrafiltration according to the second filtration step ii) of process step b), a circulating volume of from 0.5 to 3 l/min, a filtration rate of from 4 to 6 ml/min and a transmembrane pressure of from 8 to 12 psi are used.

Especially preferably, in the cross-flow ultrafiltration according to filtration step ii) of process step b), a circulating volume of from 1 to 2 l/min, a filtration rate of 5 ml/min and a transmembrane pressure of 10 psi are used. The surface area of the filter is in that case preferably 700 cm$^2$ with a 1 kD cut off.

In order to increase the yield of interleukin-8, in addition, the cell debris obtained in the first filtration step i) of process step b).

a) may first be adjusted with urea to an 8M urea solution, then b) the urea solution may be subjected to a two-fold high-pressure homogenisation in order to solubilise undissolved interleukin-8 and finally c) the product so obtained may be further purified in accordance with process steps c), d) and e).

The 8M urea solution mentioned in a) and b) is preferably adjusted to a pH optimum of 9.5.

The high-pressure homogenisation carried out in b) is carried out at a pressure of from 2000 to 10,000 psi and in from 1 to 6 cycles, preferably at a pressure of from 4000 to 8000 psi and in from 1 to 3 cycles, and especially preferably at a pressure of 6000 psi and in 2 cycles.

The interleukin-8 purified by way of the process of the invention may be used for research, treatment and diagnostic purposes.

In particular, the process of the invention for the purification of interleukin-8 is a very economical process that is suitable for use under GMP conditions, that is to say for interleukin-8 production conforming to GMP.

The yield is approximately 50%, based on the soluble portion. That is extremely high in comparison with other commercial purification methods for the production of bacterially expressed recombinant proteins in conformity with GMP and is more than satisfactory for economic use. Accordingly, a clear advantage is to be observed in comparison with conventional processes in which several chromatography steps on a liter scale are necessary to obtain the same result. Theoretically, under the conditions in conventional processes using at least 4 chromatography steps with DMF materials and yields of on average 80% per step, the yield can be estimated to be $0.8^4=0.41$, or 41%. Entrainment losses as a result of removing the cell debris and DNA and losses due to re-buffering have not been taken into account in that estimate. 10 to 20% are spoken of as acceptable yields for good commercial working-up of a bacterially expressed protein under GMP conditions.

As far as the material costs incurred in the production are concerned, first of all a few general estimates may be cited according to which the working-up of a bacterial recombinant protein may amount to from 50 to 70% of the overall production costs. The main proportion of the working-up costs arises from the cost-intensive chromatography material. In classical methods of the kind, several chromatography columns on a liter scale are used to obtain the same yield of high-purity protein as is the case with this process. This is one of the main advantages of the process that has been developed, in as much as only one chromatography step is required to isolate high-purity protein, which, in contrast to the classical liter scales, is on a milliliter scale. There is therefore a considerable reduction of costs in comparison with classical purification processes.

Figure 1:
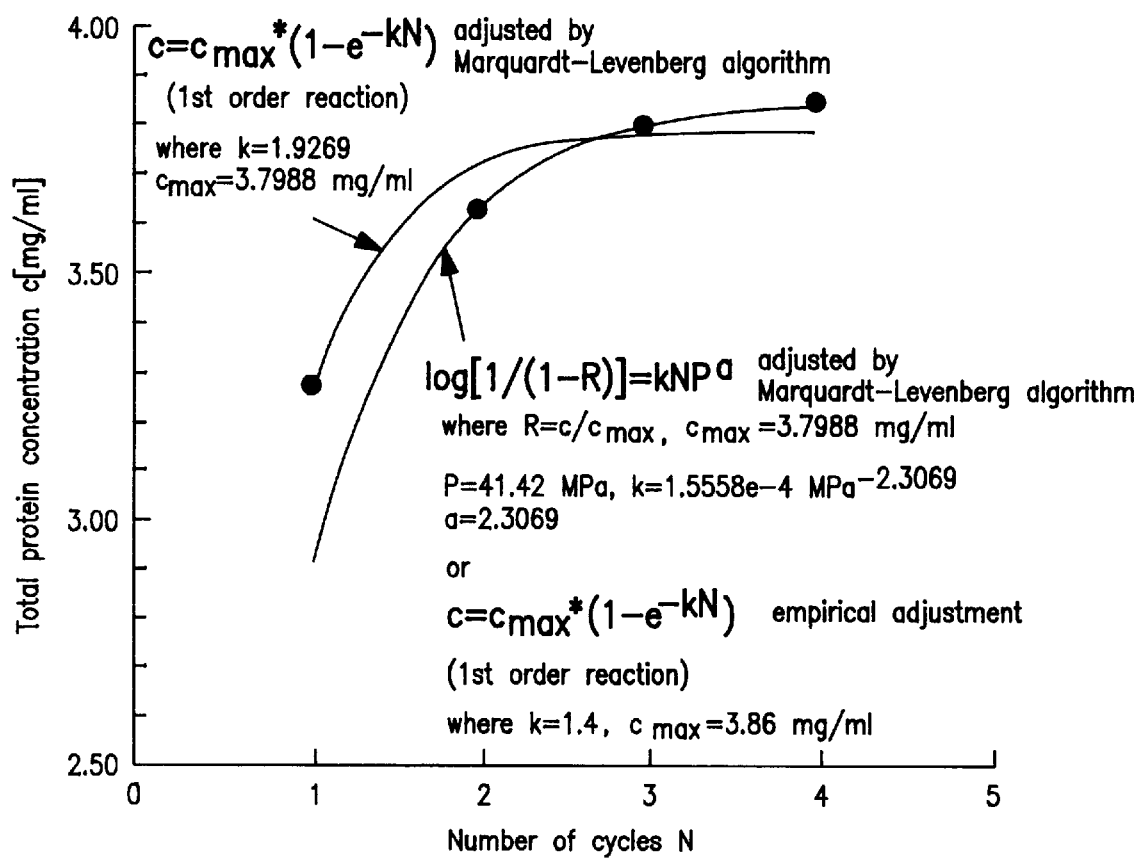
FIG. 1 shows the total protein concentration as a function of the number of cycles. All mathematical models are shown with the corresponding formulae and parameters.

The following Examples illustrate the purification process of the invention without limiting it to the Examples worked.

Working Examples

1. Cloning and Fermentation of Interleukin-8

The portion of the human interleukin-8 gene that codes for the 72 amino acid form of the protein was inserted into the plasmid pMS119EH(L). The resulting expression vector pIL8/tac was transformed into the strain E. coli TG1. The interleukin-8 was expressed in the E. coli clone TG1 (pIL8/tac) so obtained. The fermentation conditions are as follows:

20 µl were taken from an E. coli TG1 (pIL8/tac) continuous culture in glycerol at −70° C. and incubated for 48 hours at 37° C. in an agar culture with L-medium (10 g/l tryptophan (Difco), 5 g/l yeast extract (Difco), 10 g/l NaCl) and 200 mg/l ampicillin. The colonies were then rinsed off with 5 ml of L-medium. 100 µl of that culture were used to inoculate a 500 ml shaking flask containing 100 ml of L-medium. That first preculture was incubated for 16 hours at 37° C. at a shaking frequency of 180 rev/min. 10 ml of that preculture were used to inoculate the second preculture in a 2 liter shaking flask containing 1000 ml of L-medium. Incubation was carried out for 48 hours under the conditions mentioned above. 1000 ml of that second preculture were used to inoculate a 300 liter fermenter containing 200 liters of L-medium. The fermenter was stirred at 150 rev/min at 28° C. and aerated at 5 $m^3$/h. After 4 hours' fermentation, interleukin-8 expression was induced by the addition of 0.25 mmol/l IPTG, and fermentation was continued for a further 8 hours. The bacterial cells were then killed by adding octanol to a concentration of 0.1%. After the addition of octanol, the batch was stirred for 2 minutes at 45 rev/min and incubated for a further 5 minutes without stirring. The cells were harvested using a separator at 6600×g and 200 l/h and were concentrated from 200 liters to 7 liters. A bacterial cell pellet was obtained from those 7 liters by means of centrifugation.

2. Purification of Interleukin-8

2.1 Cell Lysis by High-Pressure Homogenisation (Process Step a)

423.35 g of cell mass (moist weight) were resuspended in 50 mM NaCl, 20 mM TRIS, pH 8.0 to give a final volume of 1730 ml and lysed by means of high-pressure homogenisation, the lysing of the resuspended cell mass being carried out in 4 cycles at a pressure of 6000 psi. The cell lysis was analysed by means of total protein determination, SDS-PAGE and ELISA. The behaviour of the total protein concentration as a function of the number of cycles in the high-pressure homogenisation is shown in FIG. 1. Looking at the concentration of the soluble total protein, it can be seen that the cell lysis is a first order reaction. The curve of the total protein concentration shows a marked decrease in steepness as the number of cycles increases. That points to an adequate cell lysis in the 4 cycles preferably chosen. It is furthermore possible to find an empirical adjustment to describe the cell lysis. The interleukin-8 concentration exhibited in the individual cycles only a slight change of 0.15 mg/ml after the 1st cycle to 0.17 mg/ml after the 4th cycle. In SDS-PAGE, a better separation effect was observed between the individual bands with increasing number of cycles, which can probably be attributed to a fragmentation of the DNA. The total amount of soluble protein was determined by the BCA method as being 6643.2 mg. The interleukin-8 portion of that amount corresponds, at a cautious estimate, to 4.4%.

2.2 Molecular Weight Exclusion by Repeated Cross-Flow Ultrafiltration (Process Step b)

The complete homogenisate of the cell lysate from process step a) was subjected to cross-flow ultrafiltration using a membrane having a cut off of 3 kD. The filtrate obtained was further treated by the same technique at a cut off of 1 kD. The 3 kD ultrafiltration was carried out in two phases, the filtration being carried out with a 3 kD NMWL (nominal molecular weight limit) modified PES membrane with a surface area of the filter of 2100 $cm^2$. The operating conditions selected were as follows:

filtration buffer: 5 mM EDTA, 50 mM NaCl, 20 mM TRIS. pH 9.5

| first phase: | circulating volume: | 2–3 l/min |
| | filtration rate | 6.3 ml/min |
| | transmembrane pressure | 10 psi |

After two volume changes, the filtration conditions were increased.

| second phase: | circulating volume: | 4–5 l/min |
| | filtration rate | 12.7 ml/min |
| | transmembrane pressure | 35 psi |

8620 ml of filtrate I and 1110 ml of retentate I were obtained. Analysis of the total protein by means of BCA revealed that, of the original 6643.2 mg of total soluble protein from the cell lysis, 2508.6 mg could still be re-found in retentate I and 2293.3 mg in filtrate I. Analysis of the soluble interleukin-8 revealed, after analytical HPLC using a reversed phase C4 column, that the concentration in retentate I and filtrate I was below the detection limit of less than 0.005 mg/ml. Further analysis by means of the ELISA technique revealed a concentration in retenate I of 0.002 mg/ml interleukin-8 (2.2 mg of interleukin-8).

Filtrate I was further treated with a 1 kD filtration. The 1 kD cross-flow ultrafiltration was carried out with a 1 kD NMWL (nominal molecular weight limit) modified PES membrane with a surface area of the filter of 700 cm$^2$. The operating conditions selected were as follows:

| circulating volume: | 1–2 l/min |
| filtration rate | 5.0 ml/min |
| transmembrane pressure | 10 psi |

The 8620 ml of filtrate I were concentrated to 600 ml of retentate II, producing 8020 ml of filtrate II. Analysis of retentate II by means of SDS-PAGE revealed an intense band in the molecular weight range of interleukin-8. Two further substantially weaker bands could be detected in the molecular weight range below interleukin-8. The purity of the interleukin-8 based on the total protein could be estimated roughly from the HPLC reversed phase elution profile as being 25%. N-terminal sequencing of interleukin-8 in retentate II in accordance with Edman similarly confirmed the purity. Further analysis to determine the concentration by means of the ELISA technique revealed for retentate II a concentration of 0.31 mg/ml interleukin-8 (186 mg of interleukin-8), filtrate II having a concentration of less than 0.0001 mg/ml interleukin-8 (<0.8 mg of interleukin-8). A re-finding rate of 63.2% with a purity of >25% after one pretreatment was determined.

2.3 High-Resolution Purification by Means of Cation-Exchange Chromatography (Process Step c)

A 45 ml CM-Sepharose column (XK26 column with FPLC system) was charged with 600 ml of retentate II, at a load of 90% capacity. The chromatography programme of the 45 ml CM-sepharose column is shown in the following Table:

| time [min] | chromatography step | solvents | flow rate [ml/min] |
| --- | --- | --- | --- |
| 0 | equilibration | 50 mM NaCl, 20 mM TRIS, pH 9.5 | 4.5 |
| 33 | charging | retentate II, 50 mM NaCl, pH 9.5 | 4.5 |
| 166 | washing | 50 mM NaCl, 20 mM TRIS, pH 9.5 | 4.5 |
| 333 | step-wise elution | 300 mM NaCl, 20 mM TRIS, pH 9.5 | 1.5 |
| 363 | regeneration | 1000 mM NaCl, 20 mM TRIS, pH 7.5 | 4.5 |
| 393 | regeneration | 0.1M NaOH | 4.5 |
| 423 | storage | 20% ethanol | 4.5 |
| 460 | end | — | 0.0 |

Analysis was carried out by means of reversed phase C4—HPLC and revealed a yield of more than 90%; no accompanying protein could be detected any longer. As the interleukin-8 eluate from the step-wise elution, a total of 173.4 mg of interleukin-8 were obtained according to analytical reversed phase C4—HPLC. The concentration of the eluate was, at 2.1 mg/ml, relatively high and no accompanying proteins could be detected any longer. Since endotoxins and DNA also are usually separated off during chromatography with a weak cation-exchanger, the interleukin-8 eluate was examined for purity (SDS-PAGE with overloading of the gel) and endotoxins (LAL test). Accompanying proteins also could not be detected after an overloaded SDS-PAGE with Coomassie protein staining. The endotoxin removal proved to be very effective. The concentration of endotoxin was, at less than 1.5 pg/$\mu$g of interleukin-8, below the limit of detection. The eluate was conditioned and subjected to a final product control.

2.4 Dialysis (Process Step d)

The interleukin-8 eluate was dialysed against PBS and adjusted to a concentration of 1.00 mg/ml. The dialysis was carried out at a membrane cut off of 3.5 kD. The interleukin-8 eluate was dialysed over a period of 1, 2.5 and 20 hours, each time against 5 liters of pyrogen-free PBS buffer. After dialysis, 141.7 mg of interleukin-8 could be re-found, which corresponds to a yield of 82%. The concentration was adjusted after the dialysis to 1.00 mg/ml interleukin-8 using pyrogen-free PBS buffer and verified with the Pierce BCA Protein Assay using BSA as the reference protein.

2.5 Lyophilisation (Process Step e)

After establishing a concentration of 1.00 mg/ml interleukin-8 solution in PBS, lyophilisation was carried out. For that purpose, the solution was divided between suitable small bottles in aliquots of 1.00 ml (1.00 mg of interleukin-8 per bottle) and deep-frozen at −70° C. After 12 hours at −70° C., lyophilisation was carried out for 36 hours. The sample bottles were sealed and stored at −70° C. A sample selected at random was subjected to end product control.

3. Yield of the Purification Process

The yield of the purification process of the invention is approximately 50%. That is a surprisingly high yield value for a bacterially expressed protein. The following Table summarises the analysis of the purification process:

| step | method | amount | yield per step | yield total* |
|---|---|---|---|---|
| cell harvest | centrifugation | 423.5 g of cell pellet (ww) from 200 l of E. coli fermentation | — | — |
| cell lysis | high-pressure homogenisation | 294.1 mg of soluble interleukin-8 | 100.0% | 100.0% |
| pre-purification with preparation for chromatography | double cross-flow ultra-filtration | 186.0 mg of soluble interleukin-8 | 63.2% | 63.2% |
| fine purification | ion-exchange chromatography | 173.4 mg of soluble interleukin-8 | 93.2% | 59.0% |
| conditioning | dialysis | 141.7 mg of soluble interleukin-8 | 81.7% | 48.2% |

*based on 294.1 mg of soluble interleukin-8 of the cell lysate.

Optimisation experiments in the double cross-flow ultrafiltration showed that the yield of 63.2% can be increased to more than 80%. Accordingly, the optimised purification process can provide yields of up to 65%.

4. Production Properties of the Process

For product control, tests were carried out on the pure end product with regard to identification, concentration, purity, endotoxin content and biological activity, all of which conformed to FDA specifications for GMP production for human use, as follows:

4.1 Identification

N-Terminal Sequencing according to Edman (1950)

The required sequence of the interleukin-8 could be confirmed unequivocally.

Dot Blot with Poly- and Mono-Clonal Interleukin-8 Antibodies

The dot blot revealed a direct linear relationship between signal intensity and concentration of the purified charge.

4.2 Concentration

Pierce BCA Protein Assay

Determination of the total protein concentration using the Pierce BCA Protein Assay and BSA as the reference protein gave 1.00 mg/ml.

4.3 Purity

HPLC Reversed Phase

In the HPLC reversed phase test for foreign protein by means of a C4 column, no accompanying protein could be detected at 214 nm.

SDS-PAGE with Silver Staining

SDS-PAGE with silver staining also revealed only one interleukin-8 band. Further bands could not be discovered.

SDS-PAGE with Coomassie staining and band intensity measurement

Analysis of the SDS-PAGE with Coomassie staining and subsequent band intensity measurement gave a purity of more than 99% for the purified charge.

4.4 Endotoxins

LAL test

The LAL test showed an endotoxin content of less than 1.5 pg/μg of interleukin-8 at a concentration of 1.00 mg/ml interleukin-8.

4.5 Biological Activity

Chemotactic neutrophil reaction

The $ED_{50}$, determined by the chemotactic neutrophil reaction, was 0.84 mmol/l.

5. Solubilisation of the interleukin-8 Remaining in the Cell Debris

The cell debris that had been stored at −70° C., lysed by means of high-pressure homogenisation and treated using 3 kD filtration (see 2nd purification of interleukin-8) was "thawed" in ice, warmed to room temperature and dissolved by thorough mixing with crystalline urea to give a final concentration of 8M urea. The pH value was 9.5. Two-fold high-pressure homogenisation was then carried out using a homogeniser, the 8M urea suspension being subjected to two cycles at a pressure of 6000 psi. The individual stages were analysed by means of the interleukin-8 ELISA test. The following Table shows schematically the individual steps of the interleukin-8 solubilisation on a commercial scale and the results thereof:

| step | concentration [mg/ml] | volume [ml] | amount of interleukin-8 released [mg] | amount of interleukin-8 released [%*] |
|---|---|---|---|---|
| after cross flow ultra-filtration | 0.002 mg/ml | 1110 ml | 2.2mg | 0.7% |
| after thawing | 0.008 mg/ml | 1110 ml | 8.9mg | 3.0% |
| after urea addition | 0.668 mg/ml | 1500 ml | 102.0mg | 34.7% |
| after 1st homogenisation | 0.066 mg/ml | 1800 mg | 118.8mg | 40.4% |
| after 2nd homgenisation | 0.056 mg/ml | 2000 ml | 112.0mg | 38.1% |
| after 12 hours and 1:1 dilution | 0.057 mg/ml | 4000 ml | 228.0mg | 77.5% |

*based on the soluble portion (294.1 mg of interleukin-8)

After the last stage of the commercial solubilisation process, 228.0 mg of interleukin-8 were obtained. It was found that, in the commercial reaction process, the urea addition and the 12-hour urea treatment have the greatest influence on the solubilisation. The two-fold homogenisation, on the other hand, provided only a slight increase in the interleukin-8 concentration.

Further tests showed that higher yield values are to be obtained by a longer incubation of the 8M urea solution at pH 9.5. On a laboratory scale, from twice to three times the yield could be obtained with urea treatment of 24, 36 and 48 under the same conditions.

After that treatment, the 8M urea solution was adjusted to a 4M urea concentration with deionised $H_2O$ (millipore Q system) (1:1 dilution) and again subjected to 3 kD filtration, the resulting filtrate III being further treated by 1 kD filtration in accordance with the procedure described above. Filtration of retentate I was carried out in two stages. In the first stage, the 4M urea solution was concentrated and, in the second stage, was filtered with 5 mM EDTA, 50 mM NaCl, 20 mM TRIS, pH 9.5.

filtration buffer: 5 mM EDTA, 50 mM NaCl, 20 mM TRIS. pH 9.5

| first phase: | circulating volume: | 2–3 l/min |
|---|---|---|
| | filtration rate | 6.3 ml/min |
| | transmembrane pressure | 10 psi |

After two volume changes, the filtration parameters were increased.

| | | |
|---|---|---|
| second phase: | circulating volume: | 4–5 l/min |
| | filtration rate | 18.7 ml/min |
| | transmembrane pressure | 35 psi |

Figure 2:
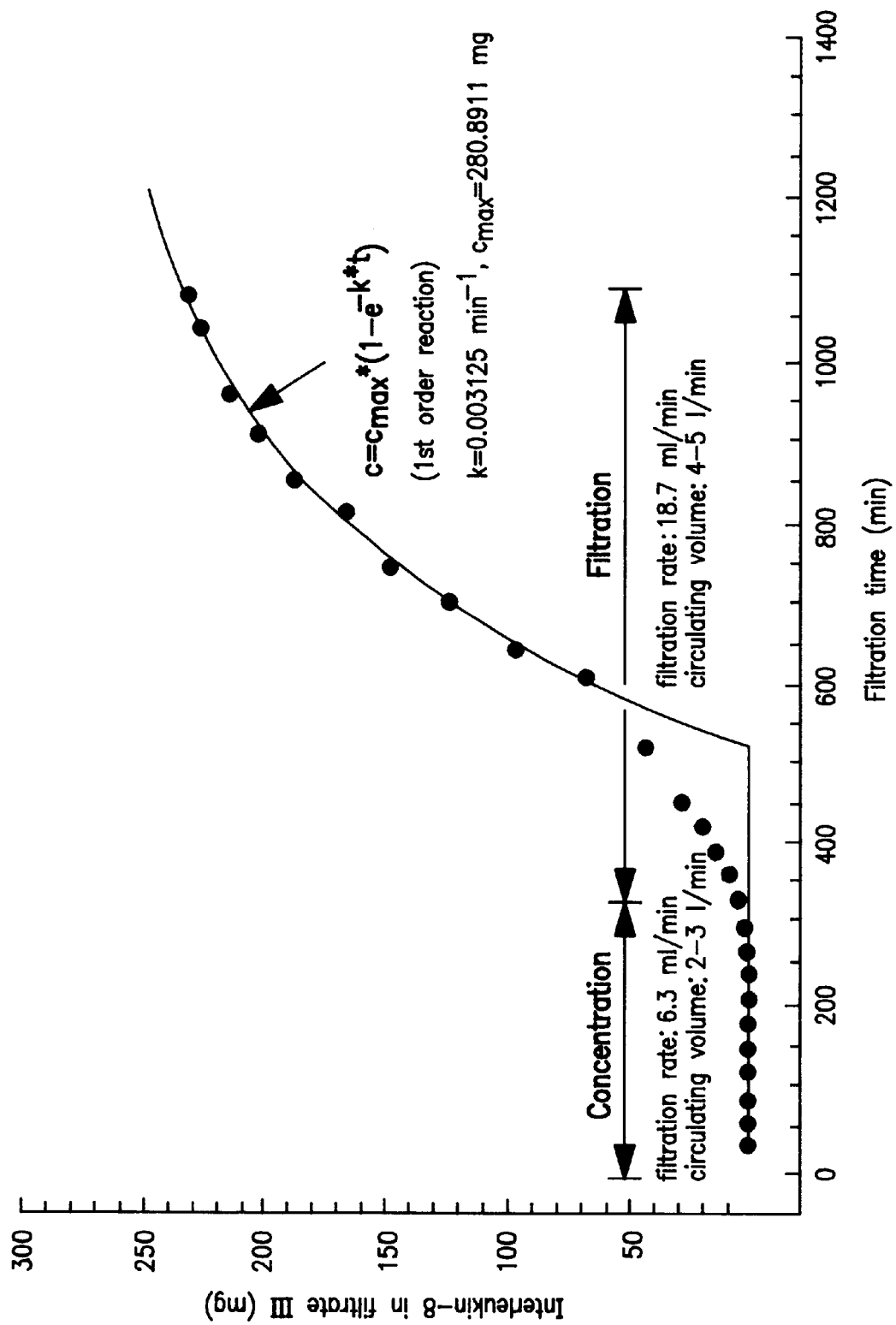
FIG. 2 shows the total amount of interleukin-8 in filtrate III over time.

The amount of interleukin-8 in filtrate III was analysed by means of the ELISA technique. The results are shown in FIG. 2. A sigmoid curve is found for the filtration behaviour, a region of transition first of all occurring upon increasing the operating parameters to the filtration step. Thereafter, the image of the 1st order reaction is produced for the filtration behaviour.

The total amount of solubilised interleukin-8 in filtrate III that could be separated from retentate I in 18 hours by means of the 3 kD filtration was 232.0 mg at a concentration of 0.015 mg/ml. Filtrate III was further treated by 1 kD filtration. Analysis by means of reversed phase C4-HPLC revealed, after concentration of 7815 ml of filtrate III to 1250 ml of retentate IV, a concentration of 0.087 mg/ml interleukin-8 (109.0 mg of interleukin-8). That corresponds to a yield of more than 90%. Filtrate IV, at a concentration of less than 0.005 mg/ml interleukin-8, was below the limit of detection. It will be seen that the total yield of interleukin-8 can be almost doubled by that solubilisation step.

What is claimed is:

1. A process of the purification of interleukin-8 from cells which contain interleukin-8, comprising:
   a) lysing cells in a buffered solution,
   b) treating the resulting lysate by means of molecular weight exclusion by repeated cross-flow ultrafiltration in such a manner that
      i) in the first filtration step interleukin-8 is separated from larger accompanying components and
      ii) in the second filtration step, interleukin-8 is separated from smaller components,
   c) subjecting the to high-resolution purification by means of cation-exchange chromatography, wherein the application and elution pH value is selected to be sufficiently high that the highly positively charged interleukin-8 can just bind,
   d) exchanging the solution of the interleukin-8 eluate from process step c) by gel filtration, dialysis or ultrafiltration, and
   e) lyophilizing the interleukin-8 solution obtained via process step d).

2. The process according to claim 1, wherein, in the cross-flow ultrafiltration in the first filtration step i) of process step b), the cut off of the membrane is below the molecular weight of interleukin-8.

3. The process according to claim 2, wherein the cross-flow ultrafiltration in the first filtration step i) is carried out at a cut off of 3 kD.

4. The process according to claim 1, wherein, in the cross-flow ultrafiltration in the second filtration step ii) of process step b), the cut off of the membrane is less than the molecular weight of interleukin-8.

5. The process according to claim 4, wherein the cross-flow ultrafiltration in the second filtration step ii) of process step b) is carried out at a cut off of 0.1 to 1.5 kD.

6. The process according to claim 5, wherein the cross-flow ultrafiltration in the second filtration step ii) of process step b) is carried out at a cut off of 1 kD.

7. The process according to claim 1, wherein, in process step a), the cell lysis is effected by high-pressure homogenization.

8. The process according to claim 1, wherein, in process step a), the cell lysis is effected enzymatically or chemically.

9. The process according to claim 1, wherein, in step a), 1 to 6 cycles of cell lysis are effected at a pressure of 2000 to 15,000 psi.

10. The process according to claim 9, wherein, in step a), 3 to 5 cycles of cell lysis are effected at a pressure of 5000 to 7000 psi.

11. The process according to claim 9, wherein 4 cycles of cell lysis are effected at a pressure of 6000 psi.

12. The process according to claim 1, wherein the cells lysed are cells of a prokaryotic expression system.

13. The process according to claim 12, wherein the cells lysed are E. coli cells.

14. The process according to claim 1, wherein the cells lysed are cells of eukaryotic expression system.

15. The process according to claim 14, wherein the cells lysed are yeast cells, insect cells or mammalian cells.

16. The process according to claim 15, wherein, the yeast cells are *Pichia pastoris* and the insect cells are Baculovirus-transfected insect cells.

17. The process according to claim 15, wherein the mammalian cells are transformed Chinese Hamster Ovary (CHO) or Baby Hamster Kidney (BHK) cells.

18. A process for the purification of interleukin-8 from the milk of a transgenic animal, which milk contains interleukin-8, comprising:
   a) treating the milk by means of molecular weight exclusion by repeated cross-flow ultrafiltration in such a manner that
      i) in the first filtration step interleukin-8 is separated from larger accompanying components and
      ii) in the second filtration step, interleukin-8 is separated from smaller components,
   b) subjecting the filtrate from process step a) to high-resolution purification by means of cation-exchange chromatography, wherein the application and elution pH value is selected to be sufficiently high that the highly positively charged interleukin-8 can just bind,
   c) exchanging the solution of the interleukin-8 eluate from process step b) by gel filtration, dialysis or ultrafiltration, and
   d) lyophilizing the interleukin-8 solution obtained via process step d).

19. The process according to claim 1, wherein, in process step c), the application and elution pH values are from pH 8 to pH 10.

20. The process according to claim 19, wherein the application and elution pH values are pH 9.5.

21. The process according to claim 1, wherein the cross-flow ultrafiltration in the first filtration step i) of process step b) is carried out in two stages.

22. The process according to claim 21, wherein, in the cross-flow ultrafiltration, a circulating volume of from 1 to 10 l/min, a filtration rate of from 1 to 20 ml/min and a transmembrane pressure of from 1 to 150 psi are used both in the first stage and in the second stage.

23. The process according to claim 21, wherein, in the cross-flow ultrafiltration, a circulating volume of 1 to 4 l/min, a filtration rate of from 5 to 8 ml/min and a transmembrane pressure of 1 to 20 psi are used in the first phase and a circulating volume of 3 to 6 l/min, a filtration rate of from 10 to 15 ml/min and a transmembrane pressure of 20 to 50 psi are used in the second phase.

24. The process according to claim 23, wherein, in the ultrafiltration, a circulating volume of 2 to 3 l/min, a filtration rate of 6.3 ml/min and a transmembrane pressure of 10 psi are used in the first stage, and a circulating volume of 4 to 5 l/min, a filtration rate of 12.7 ml/min and a transmembrane pressure of 35 psi are used in the second stage.

25. The process according to claim 22, wherein, in the ultrafiltration, a circulating volume of 2 to 3 l/min, a filtration rate of 6.3 ml/min and a transmembrane pressure of 10 psi are used in the first stage, and a circulating volume of 4 to 5 l/min, a filtration rate of 18.7 ml/min and a transmembrane pressure of 35 psi are used in the second stage.

26. The process according to claim 1, wherein, in the cross-flow ultrafiltration in the second filtration step ii) of process step b), a circulating volume of 0.5 to 10 l/min, a filtration rate of 1 to 20 ml/min and a transmembrane pressure of 5 to 150 psi are used.

27. The process according to claim 26, in the cross-flow ultrafiltration in the second filtration step ii) of process step b), a circulating volume of 0.5 to 3 l/min, a filtration rate of 4 to 6 ml/min and a transmembrane pressure of 8 to 12 psi are used.

28. The process according to claim 26, wherein, in the cross-flow ultrafiltration, a circulating volume of 1 to 2 l/min, a filtration rate of 5 ml/min and a transmembrane pressure of 10 psi are used.

29. The process according to claim 1, further compromising treating the cell debris obtained in the first filtration step i) of process step b) by f) adjusting with urea to form an 8M urea solution, g) subjecting the urea solution to a two-fold high-pressure homogenization in order to solubilize undissolved interleukin-8, and h) further purifying the product so obtained in accordance with process steps c), d) and e).

30. The process according to claim 29, the urea solution in f) and g) has a pH of 9.5.

31. The process according to claim 29, wherein, in step g), 1 to 6 cycles of high-pressure homogenization are carried out at a pressure of from 200 to 10,000 psi.

32. The process according to claim 31, wherein, in step g), 1 to 3 cycles of high-pressure homogenization are carried out at a pressure of from 4000 to 8000 psi.

33. The process according to claim 31, wherein, in step g), 2 cycles of high-pressure homogenization are carried out a pressure of 6000 psi.

34. A method for interleukin-8 production conforming to Good Manufacturing Practice (GMP), comprising carrying out the purification process according to claim 1.

35. The process according to claim 29, wherein the urea solution in f) and g) has a pH of 8 to 10.

36. The process according to claim 18, wherein the transgenic animal is a cow or a goat.

* * * * *

UNITED STATES PATENT AND TRADEMARK OFFICE
CERTIFICATE OF CORRECTION

PATENT NO.    : 6,114,510
DATED         : September 5, 2000
INVENTOR(S)   : Scholz et al.

It is certified that error appears in the above-identified patent and that said Letters Patent is hereby corrected as shown below:

Column 11,
Line 11, reads "subjecting the to high-resolution" should read -- subjecting the filtrate from process step b) to high-resolution --;

Column 12,
Lines 4 and 7, reads "phase" should read -- stage --

Signed and Sealed this

Eleventh Day of June, 2002

*Attest:*

*Attesting Officer*

JAMES E. ROGAN
*Director of the United States Patent and Trademark Office*